(12) United States Patent
Kandori et al.

(10) Patent No.: US 10,247,789 B2
(45) Date of Patent: Apr. 2, 2019

(54) MAGNETORESISTIVE SENSOR AND GRADIOMETER

(71) Applicant: Hitachi, Ltd., Tokyo (JP)

(72) Inventors: Akihiko Kandori, Tokyo (JP); Yusuke Seki, Tokyo (JP); Ryuzo Kawabata, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 143 days.

(21) Appl. No.: 15/408,863

(22) Filed: Jan. 18, 2017

(65) Prior Publication Data

US 2017/0168123 A1 Jun. 15, 2017

Related U.S. Application Data

(62) Division of application No. 14/424,045, filed as application No. PCT/JP2012/072127 on Aug. 31, 2012, now abandoned.

(51) Int. Cl.
| | |
|---|---|
| *G01R 33/09* | (2006.01) |
| *G01R 33/022* | (2006.01) |
| *A61B 5/055* | (2006.01) |
| *A61B 5/04* | (2006.01) |
| *G01R 33/00* | (2006.01) |

(52) U.S. Cl.
CPC .......... *G01R 33/09* (2013.01); *A61B 5/04005* (2013.01); *A61B 5/055* (2013.01); *G01R 33/0041* (2013.01); *G01R 33/022* (2013.01)

(58) Field of Classification Search
CPC ........ G01R 33/09; G01R 33/41; G01R 33/22; A61B 5/4005
See application file for complete search history.

(56) References Cited

U.S. PATENT DOCUMENTS

| | | | | | |
|---|---|---|---|---|---|
| 4,616,281 | A | * | 10/1986 | Nakamura | ............. G01B 7/023 324/207.21 |
| 5,378,885 | A | * | 1/1995 | Jones, Jr. | ............... G01R 33/09 235/449 |

(Continued)

FOREIGN PATENT DOCUMENTS

| | | |
|---|---|---|
| JP | 06-180242 | 6/1994 |
| JP | 2002-311064 A | 10/2002 |

(Continued)

OTHER PUBLICATIONS

D.F. He et al., An anisotropic magneto resistive sensor with set/reset field, Review of Scientific Instruments 82, 094703 (2011).

(Continued)

*Primary Examiner* — Tung X Nguyen
*Assistant Examiner* — Dominic Hawkins
(74) *Attorney, Agent, or Firm* — Mattingly & Malur, PC

(57) ABSTRACT

An object of the invention is to reduce 1/f noise and white noise at the same time by integrally reducing noise of an MR sensor and noise of an operation circuit part. A magnetoresistive sensor according to the invention includes a plurality of magnetoresistive sensor parts each having a bridge circuit in which four magnetoresistive elements are connected, and outputs of the respective magnetoresistive sensor parts are connected in parallel to one another to an input of an amplifier circuit (see FIG. 2).

9 Claims, 9 Drawing Sheets

(56) References Cited

U.S. PATENT DOCUMENTS

| | | | | |
|---|---|---|---|---|
| 5,491,475 | A * | 2/1996 | Rouse | G08G 1/042 324/244 |
| 5,890,099 | A * | 3/1999 | Abendroth | G01C 21/28 701/530 |
| 6,169,396 | B1 | 1/2001 | Yokotani | |
| 6,304,397 | B1 * | 10/2001 | Ozue | G11B 5/0086 360/271.1 |
| 6,376,933 | B1 * | 4/2002 | Goetz | G01R 33/09 307/91 |
| 6,433,545 | B1 * | 8/2002 | Kunze | G01R 33/09 324/207.21 |
| 6,542,000 | B1 * | 4/2003 | Black | G11C 14/00 326/39 |
| 8,410,893 | B2 * | 4/2013 | Kawasaki | H01L 43/02 257/421 |
| 8,749,232 | B2 * | 6/2014 | Fu | G01R 33/096 324/252 |
| 2004/0021970 | A1 * | 2/2004 | Kondo | G11B 5/0086 360/31 |
| 2005/0150295 | A1 * | 7/2005 | Wright | G01C 17/38 73/504.04 |
| 2007/0159876 | A1 * | 7/2007 | Sugibayashi | G11C 11/16 365/158 |
| 2008/0048809 | A1 | 2/2008 | Narita | |
| 2010/0134944 | A1 * | 6/2010 | Yamamoto | H03F 3/181 361/143 |
| 2012/0166122 | A1 * | 6/2012 | Bottinelli | G01R 33/09 702/85 |
| 2018/0220927 | A1 * | 8/2018 | Kelly | G01R 33/09 |

FOREIGN PATENT DOCUMENTS

| | | |
|---|---|---|
| JP | 2003-194598 A | 7/2003 |
| JP | 2007-192722 | 8/2007 |
| JP | 2008-170368 | 7/2008 |

OTHER PUBLICATIONS

D.F. He et al., Highly sensitive anisotropic magnetoresistance magnetometer for Eddy-current nondestructive evaluation, Review of Scientific Instruments 80, 036102 (2009).

International Search Report in PCT/JP2012/072127, dated Nov. 20, 2012.

Translation of Japanese Office Action received in corresponding Japanese Application No. 2014-532675 dated Nov. 10, 2015.

* cited by examiner

[FIG. 1]
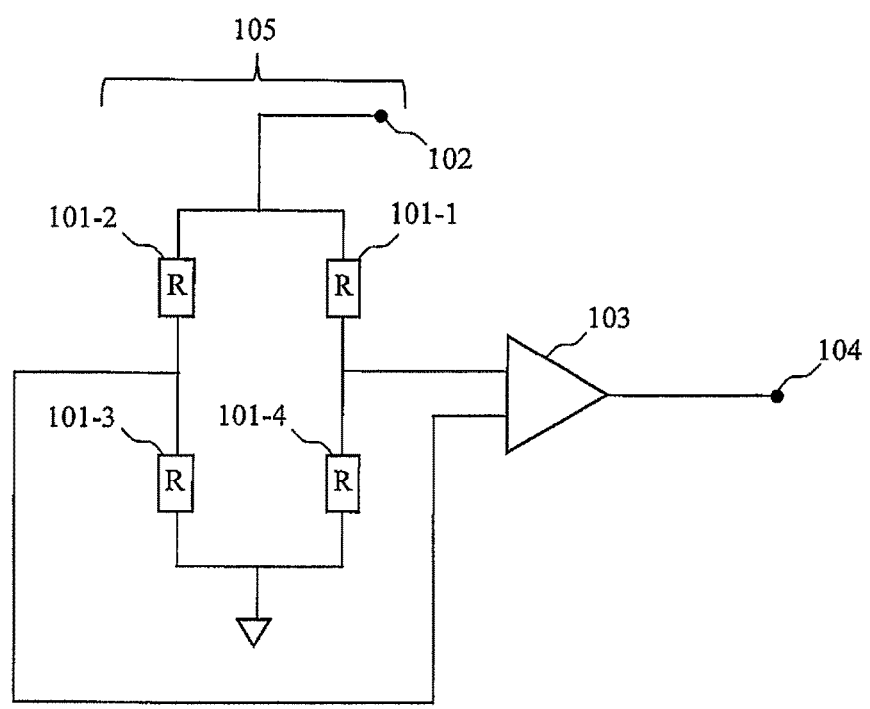

[FIG. 2]
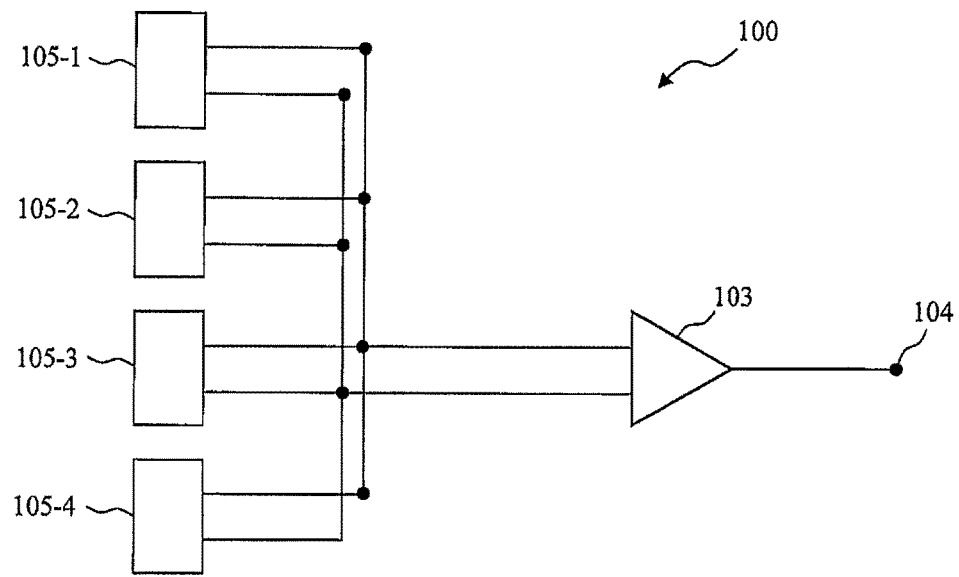
[FIG. 3]
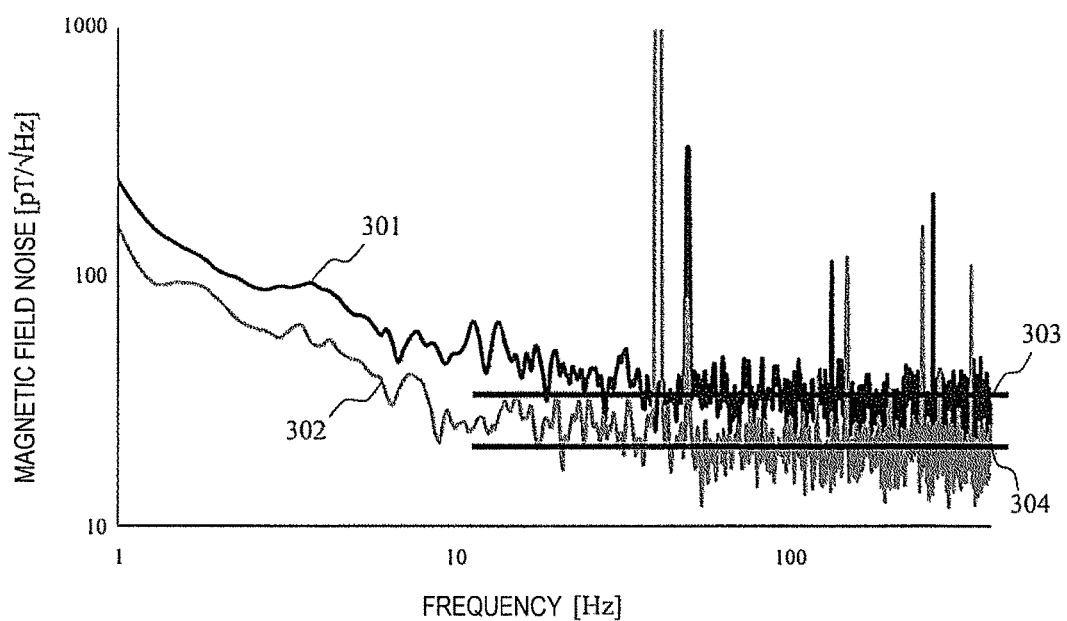

[FIG. 4A]
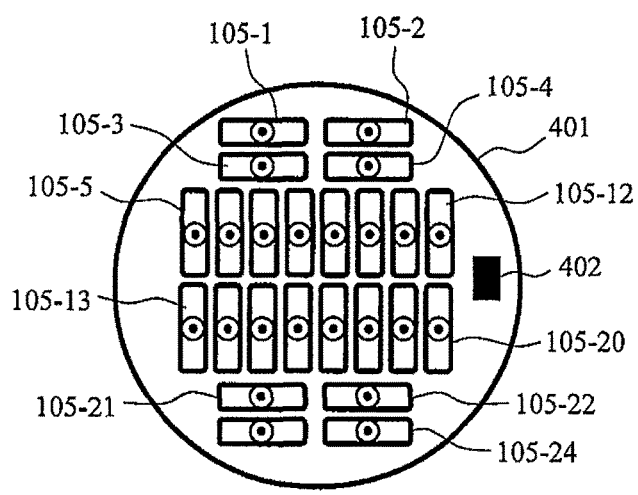
⊙ MEASUREMENT SENSITIVITY DIRECTION
(DIRECTION PERPENDICULAR
TO PLANE OF PAPER)
[FIG. 4B]
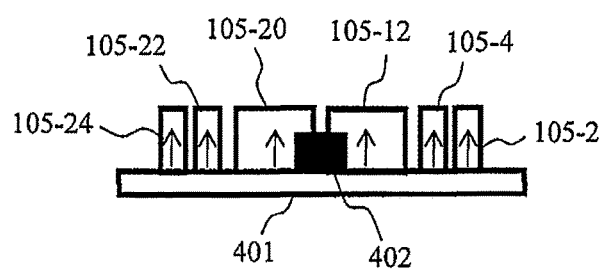
↑ MEASUREMENT SENSITIVITY DIRECTION

[FIG. 5]
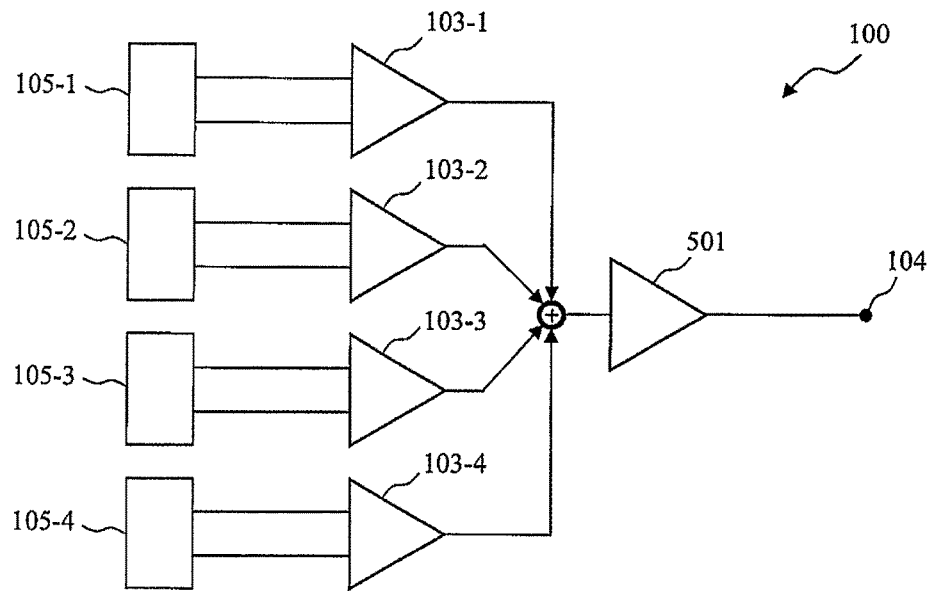
[FIG. 6]
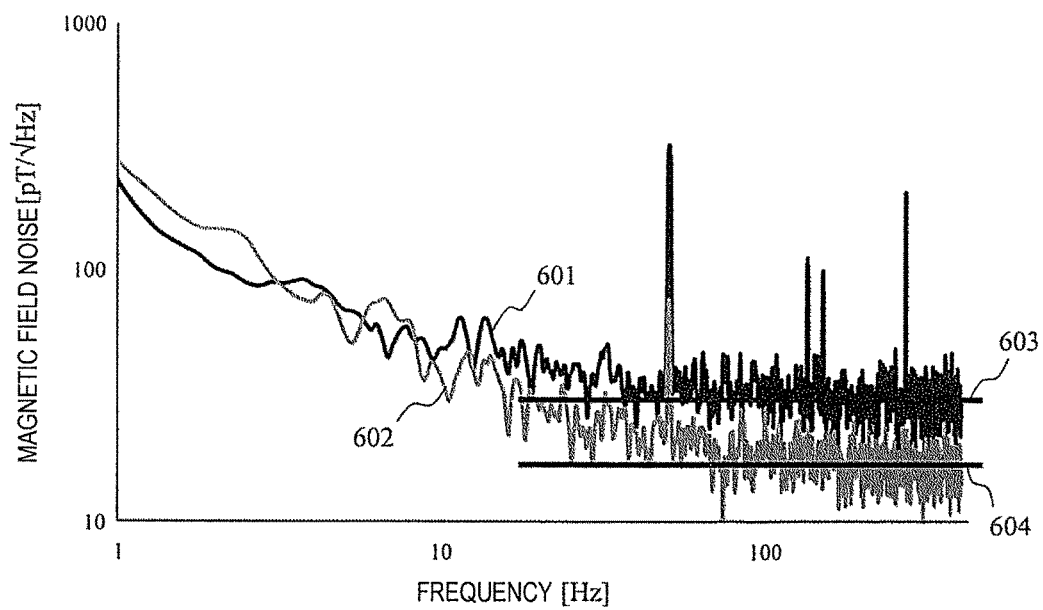

[FIG. 7]
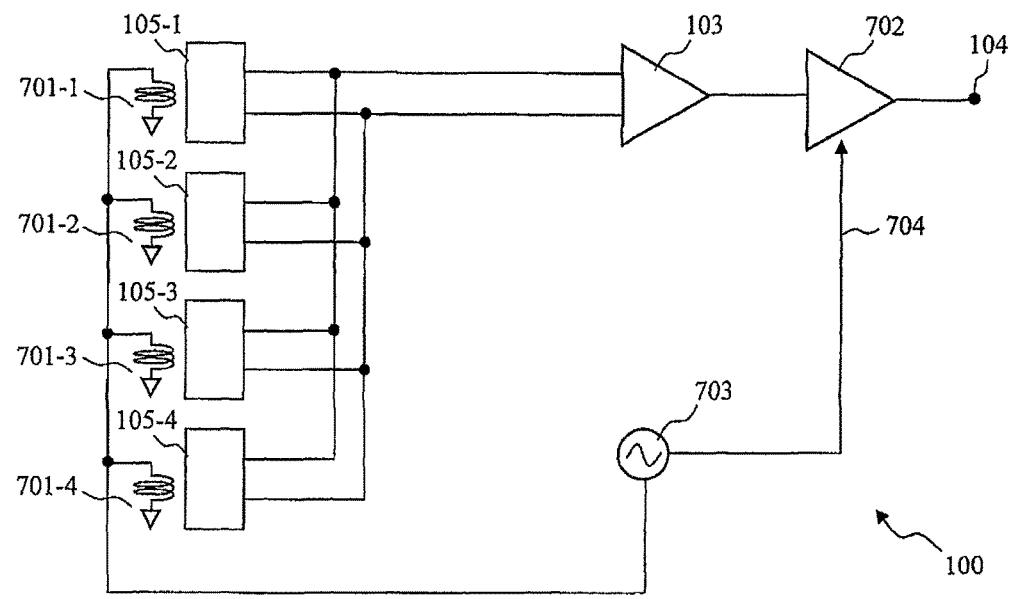
[FIG. 8]
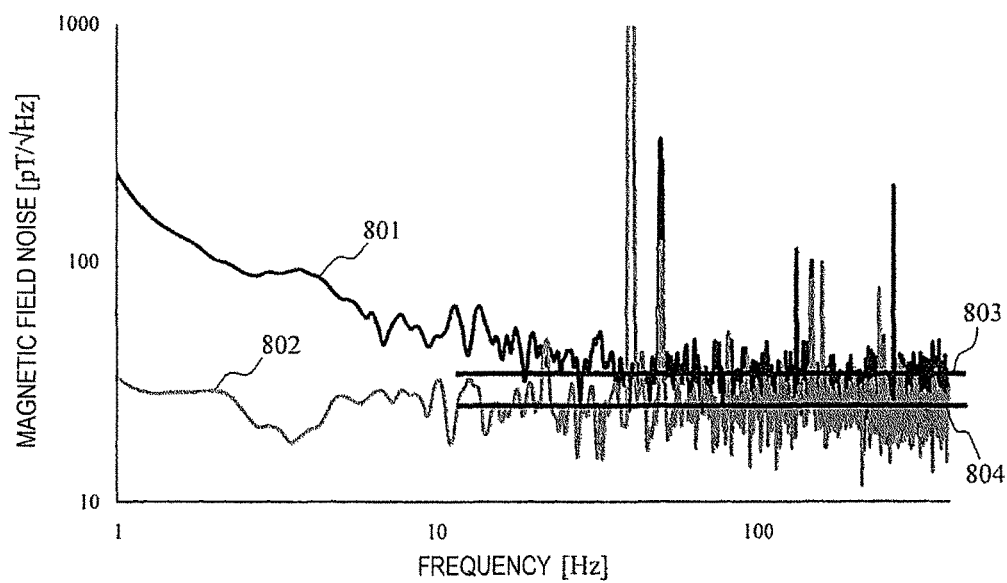

[FIG. 9]
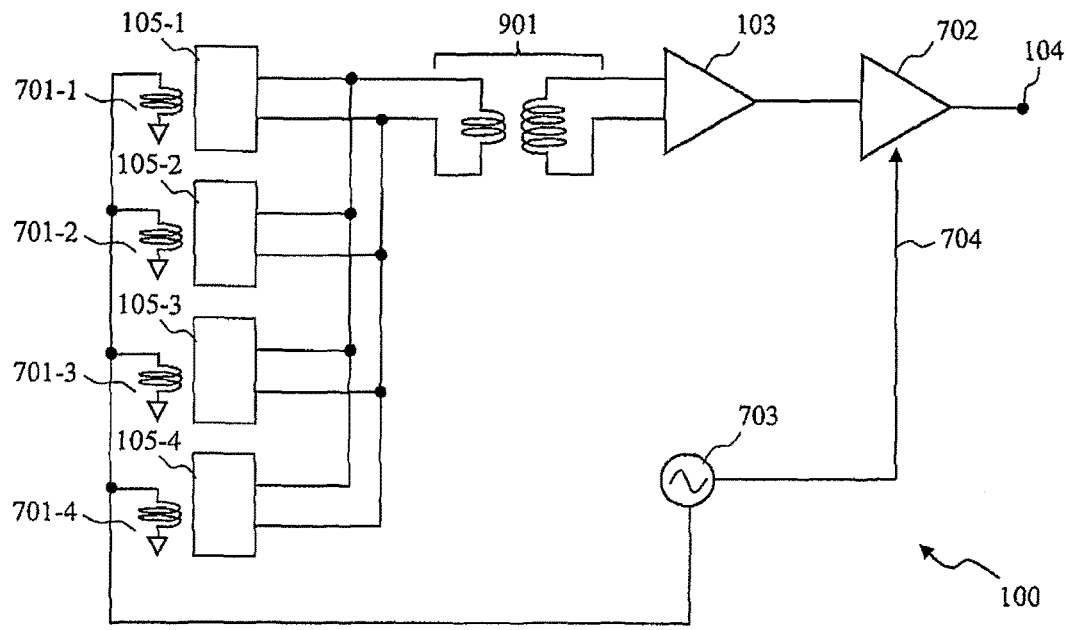
[FIG. 10]
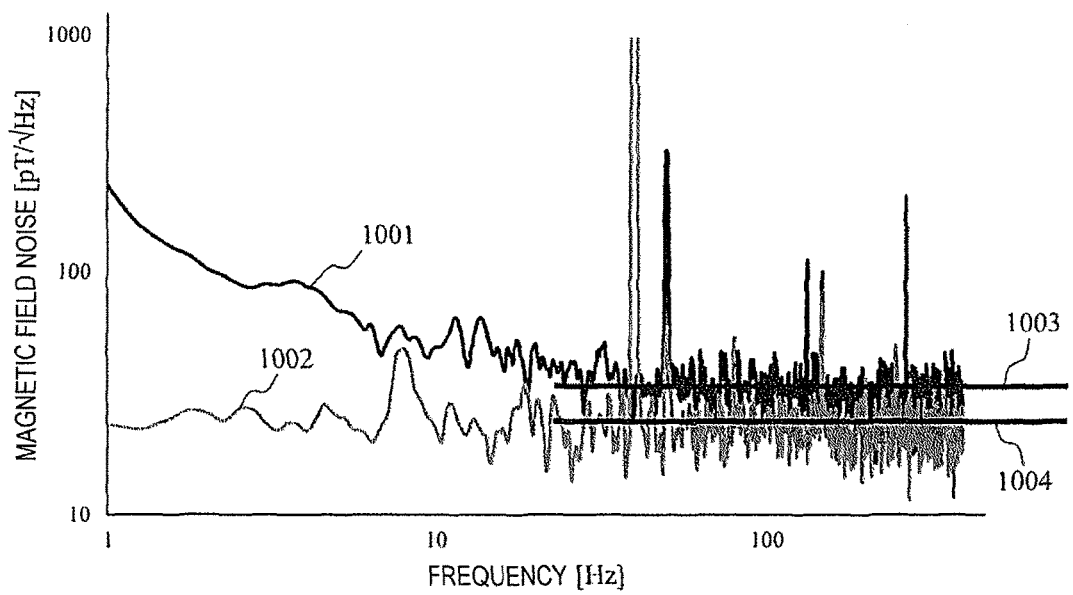

[FIG. 11]
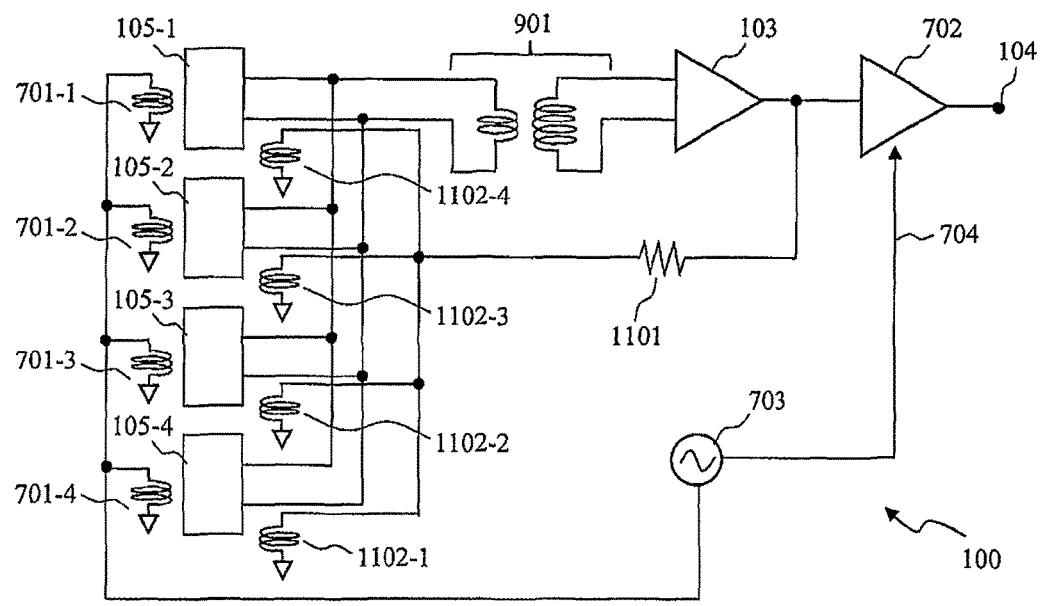
[FIG. 12]
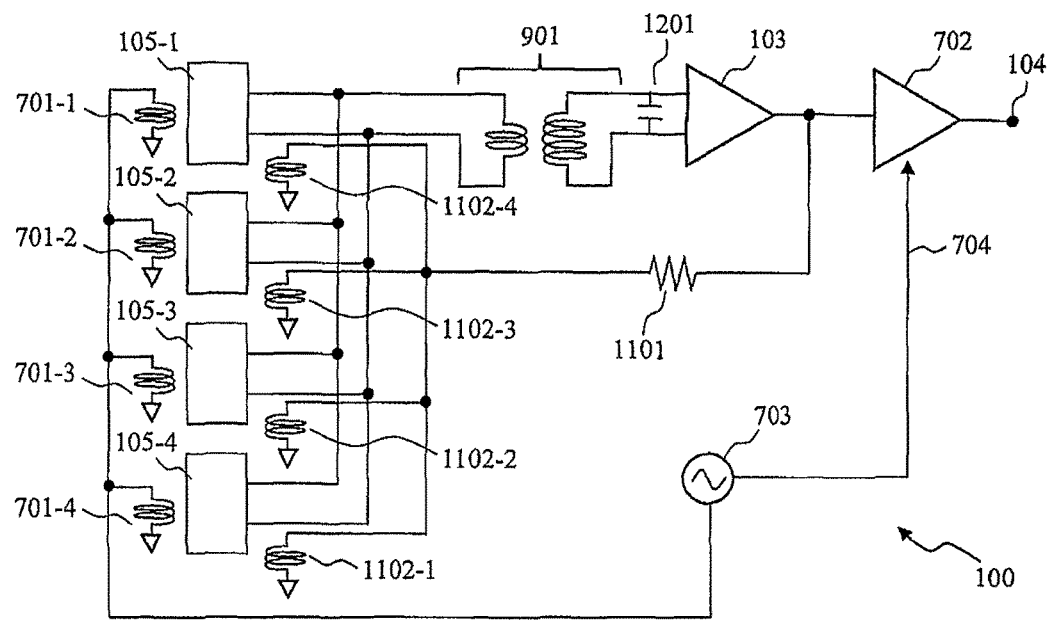

[FIG. 13]
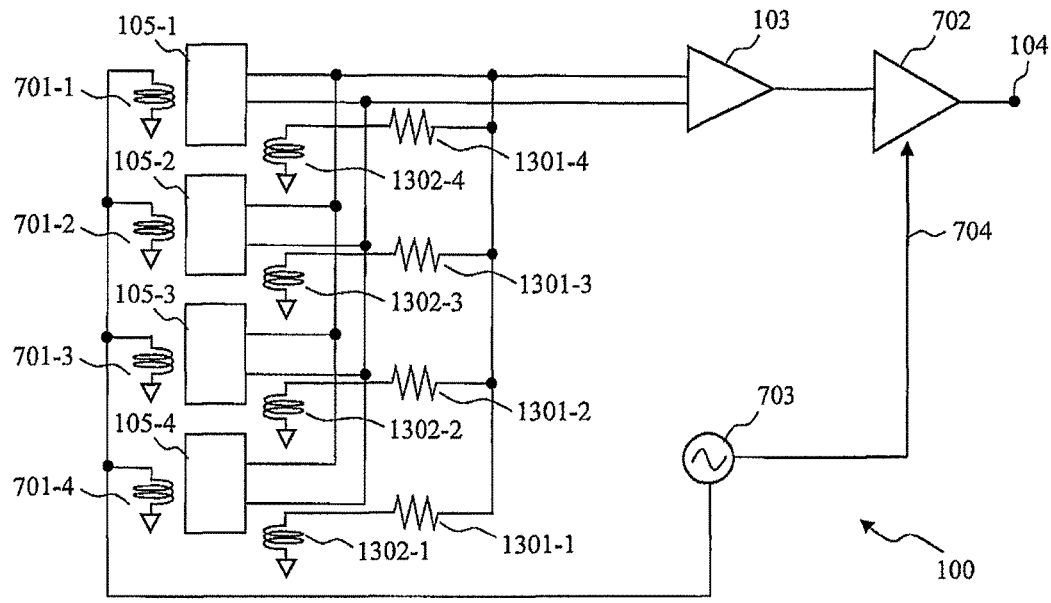
[FIG. 14]
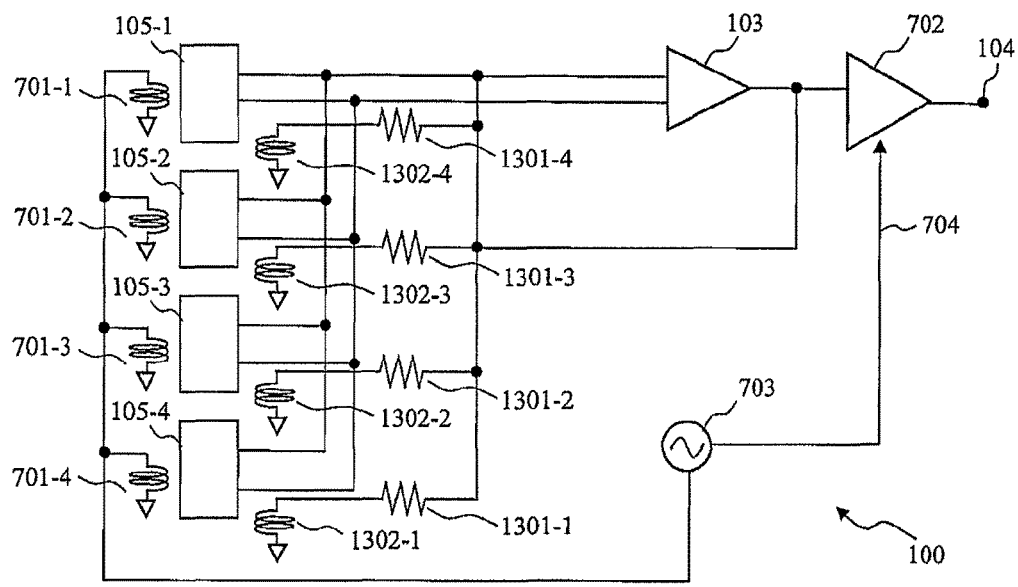

[FIG. 15]
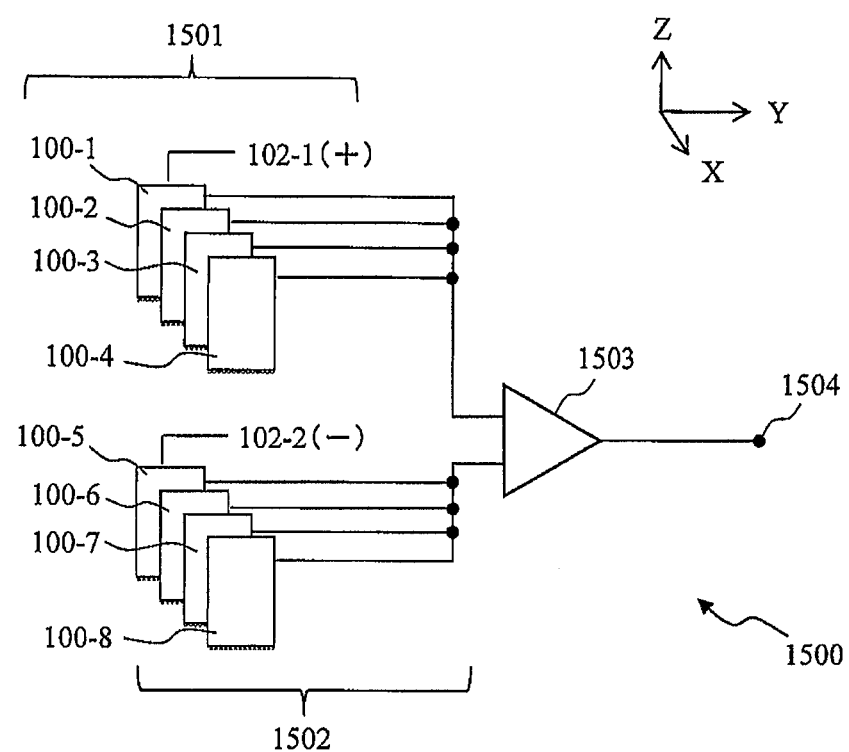

MAGNETORESISTIVE SENSOR AND GRADIOMETER

CROSS-REFERENCE TO RELATED APPLICATION

This application is a divisional application of U.S. application Ser. No. 14/424,045, filed Feb. 26, 2015, the entirety of the contents and subject matter of all of the above is incorporated herein by reference.

TECHNICAL FIELD

This invention relates to a magnetoresistive sensor and a gradiometer using the same.

BACKGROUND ART

Magnetic resistance (hereinafter, abbreviated as MR) sensors are inexpensive, small, and highly sensitive, and widely used for contactless revolution detection and position detection. The MR sensors include giant magnetoresistance (hereinafter, abbreviated as GMR) sensors, tunnel magnetoresistance (hereinafter, abbreviated as TMR) sensors, and an-isotropic magnetoresistance (hereinafter, abbreviated as AMR) sensors.

Recently, mobile devices such as cell phones and PDA (personal digital assistant) have been widespread and the mobile devices contain direction sensors using the MR sensors and may be used as navigation systems using position information by GPS (Global Positioning System). However, in adaptation of the MR sensors in the field of industrial application, high-sensitive magnetism detection technologies are not necessarily required. For example, the direction sensor detects an absolute direction with reference to geomagnetism and does not require ultrasensitive magnetism detection, and, even in encode application of revolution detection and position detection, uses a magnet as a reference signal and the ultrasensitive magnetism detection is not essential.

On the other hand, medical devices including magnetocardiograph and magnetocephalograph that detect weak and low-frequency magnetic fields generated from electrical activity of living hearts and brains (hereinafter, referred to as "biomagnetic fields") have been recently started to be used at medical sites. For detection of the biomagnetic field, a superconducting quantum interference device (hereinafter, referred to as SQUID) is used as the ultrasensitive magnetic sensor. The SQUID is a magnetic sensor using a superconductive phenomenon and has a structure with Josephson junction. Accordingly, the SQUID requires cooling by refrigerant (liquid helium or liquid nitrogen) and is placed within a cryostat in which the refrigerant is stored. Further, a configuration that does not electromagnetically affect the Josephson junction within the SQUID is required. As described above, the SQUID is the ultrasensitive magnetic sensor, but there are problems that handling is complicated and it is impossible to make the magnetic sensor sufficiently closer to the living organism because the sensor is placed within the cryostat.

In order to measure the biomagnetic field, the sensitivity of the MR sensor at the lower frequency (100 Hz or less, particularly, 30 Hz or less) containing many biologically-originated signal components is important. The noise determining the sensitivity in the low-frequency region includes two kinds of noise of white noise and 1/f noise. These two kinds of noise is not determined only by the noise generated by the MR sensor, but determined as system noise (sensitivity) by preamplifier noise and a combination with other operation circuits.

In the report on higher sensitivity of the MR sensor described in the following NPL 2, a technique of feeding back magnetic flux to the MR sensor is disclosed. In the same literature, 1/f noise including thermal fluctuation originated from the MR sensor is reduced by the feedback technique. The technology of the literature is assumed to be used in the field of non-destructive inspection and intended to stabilize operation even in severe environments (high temperature or the like).

The following NPL 1 describes that set/reset pulse is applied to the MR sensor, magnetization of magnetoresistive elements is inverted, resulting alternating-current signals are detected, and thereby, the 1/f noise originated from the MR sensor is reduced.

In the following PTL 1, as described in paragraphs, a configuration in which "element groups in which magnetoresistance-effect elements are parallel-connected are series-connected" is disclosed "in order to obtain a magnetic field detector in which sensitivity does not vary even after adjustment of the zero-point offset voltage of output". The configuration of PTL 1 suppresses variations in sensitivity and reduces 1/f noise originated from the MR sensor.

CITATION LIST

Patent Literature

PTL 1: Japanese Patent No. 4899877

Non Patent Literature

NPL 1: Rev. Sci. Instrum. 82, 094703, 2011
NPL 2: Rev. Sci. Instrum. 80, 036102, 2009

SUMMARY OF INVENTION

Technical Problems

All of the technologies described in the respective literature disclose only the reduction techniques focusing attention on the noise generated by only the MR sensors, and contains no description on the reduction of system noise. Further, in the respective literature, only the techniques of reducing 1/f noise originated from the MR sensors are disclosed, but no technique of reducing white noise as basic system noise is clearly described, or no technique of reducing 1/f noise at the same time with white noise is described.

Furthermore, the technique of parallel-connecting magnetoresistive elements described in PTL 1 requires microfabrication for parallel connection of many magnetoresistive elements in an array form, and the manufacturing facility becomes complex and problematic in view of yield and cost.

In view of the above described problems, an object of the invention is to reduce 1/f noise and white noise at the same time by integrally reducing noise of an MR sensor and noise of an operation circuit part.

Solution to Problems

A magnetoresistive sensor according to the invention includes a plurality of magnetoresistive sensor parts each having a bridge circuit in which four magnetoresistive elements are connected, wherein outputs of the respective magnetoresistive sensor parts are connected in parallel to one another to an input of an amplifier circuit.

Advantageous Effects of Invention

According to a magnetoresistive sensor of the invention, noise originated from an MR sensor may be reduced by a simple configuration.

The other problems, configurations, and advantageous effects than those described above will be clear by the following explanation of embodiments.

BRIEF DESCRIPTION OF DRAWINGS

FIG. 1 is a circuit diagram of an MR sensor in related art.

FIG. 2 is a circuit diagram of an MR sensor 100 according to embodiment 1.

FIG. 3 shows measurement results of system noise measured using an actual AMR sensor with respect to the MR sensor 100 according to embodiment 1.

FIGS. 4(a) and 4(b) exemplify an arrangement of magnetoresistive sensor parts 105.

FIG. 5 is a circuit diagram of an MR sensor 100 according to embodiment 2.

FIG. 6 shows measurement results of system noise measured using an actual AMR sensor with respect to the MR sensor 100 according to embodiment 2.

FIG. 7 is a circuit diagram of an MR sensor 100 according to embodiment 3.

FIG. 8 shows measurement results of system noise measured using an actual AMR sensor with respect to the MR sensor 100 according to embodiment 3.

FIG. 9 is a circuit diagram of an MR sensor 100 according to embodiment 4.

FIG. 10 shows measurement results of system noise measured using an actual AMR sensor with respect to the MR sensor 100 according to embodiment 4.

FIG. 11 is a circuit diagram of an MR sensor 100 according to embodiment 5.

FIG. 12 is a circuit diagram of an MR sensor 100 according to embodiment 6.

FIG. 13 is a circuit diagram of an MR sensor 100 according to embodiment 7.

FIG. 14 is a circuit diagram of an MR sensor 100 according to embodiment 8.

FIG. 15 shows a configuration of a gradiometer 1500 according to embodiment 9.

DESCRIPTION OF EMBODIMENTS

<MR Sensor in Related Art>

FIG. 1 is a circuit diagram of an MR sensor in related art. The MR sensor in related art has a bridge circuit (magnetoresistive sensor part 105) including magnetoresistive elements 101-1, 101-2, 101-3, 101-4 and detects a magnetic field by minute resistance change due to a varying magnetic field. A direct-current power source 102 applies a direct-current voltage as a drive voltage of the bridge circuit 105. A preamplifier 103 amplifies the voltage between both ends of the bridge circuit 105 and outputs it from an output terminal 104.

In the MR sensor in related art shown in FIG. 1, it is considered that thermal noise (shot noise) due to resistance components of the MR sensor becomes larger noise of the whole system and high-sensitivity detection of the magnetic field is difficult.

Embodiment 1

FIG. 2 is a circuit diagram of an MR sensor 100 according to embodiment 1 of the invention. The MR sensor 100 includes a plurality of the magnetoresistive sensor parts 105 shown in FIG. 1, and the outputs of the respective magnetoresistive sensor parts 105 are connected to the input of the preamplifier 103 in parallel to one another. In FIG. 2, the four magnetoresistive sensor parts 105-1, 105-2, 105-3, 105-4 are exemplified, however, the number of magnetoresistive sensor parts 105 is not limited to that.

When the number of parallel-connected magnetoresistive sensor parts 105 is N, the effective resistance of the parallel-connected magnetoresistive sensor parts 105 as a whole is one Nth of the resistance between both ends of the individual magnetoresistive sensor parts 105.

The thermal noise Vr of the MR sensor 100 is calculated by the following formula 1. k is the Boltzmann constant, R is the resistance between both ends of the magnetoresistive sensor part 105, and T is an absolute temperature.

$$Vr = (4kRT)^{1/2} \qquad \text{formula 1}$$

According to formula 1, the N magnetoresistive sensor parts 105 are parallel-connected and the effective resistance is made to be one Nth, and thereby, the thermal noise (shot noise) generated from the resistance of the MR sensor 100 is one $N^{1/2}$th. That is, the outputs of the plurality of magnetoresistive sensor parts 105 are parallel-connected to the input of the preamplifier 103, and thereby, the thermal noise originated from the MR sensor may be reduced and the magnetic field may be detected with high sensitivity. In FIG. 2, the case where there are the four magnetoresistive sensor parts 105 is exemplified, however, in order to exhibit sensitivity that enables measurement of the biomagnetic field, it is desirable to connect ten or more of the magnetoresistive sensor parts 105 in parallel.

FIG. 3 shows measurement results of system noise measured using an actual AMR sensor with respect to the MR sensor 100 according to the embodiment 1. Sign 301 denotes system noise measured using the configuration in FIG. 1 and sign 302 denotes system noise measured using the configuration in FIG. 2. Signs 303 and 304 denote white noise in the respective measurement results. The white noise 303 was 35 pT/Hz$^{1/2}$ and the white noise 304 was 20 pT/Hz$^{1/2}$.

According to the measurement results shown in FIG. 3, it is known that the white noise 304 is about one half of the white noise 303. That is, as is known from the theoretical value calculated by the formula 1, it is known that the four magnetoresistive sensor parts 105 are parallel-connected, and thereby, thermal noise (voltage noise) generated from the resistance of the MR sensor 100 can be reduced to be one $4^{1/2}$th=one half. Further, it is known that the thermal noise is reduced and the effect of reducing the noise as a whole is exerted, and the 1/f noise is reduced in the lower frequency region.

FIGS. 4(a) and 4(b) exemplify an arrangement of the magnetoresistive sensor parts 105. FIG. 4(a) is a top view and FIG. 4(b) is a side view. The magnetoresistive sensor parts 105 are arranged so that sensitivity directions may be the same as shown in FIGS. 4(a) and 4(b). For example, as shown in FIG. 4(a), the magnetoresistive sensor parts 105 having detection sensitivity in the direction perpendicular to the plane of paper are arranged on a substrate 401. On the substrate 401, the preamplifier 103 (not shown) is provided and power supply and signal output of the preamplifier 103 are connected to an external device through a connector part 402. The preamplifier 103 is desirably provided on the substrate 401 in view of the mounting space, however, not limited to that.

FIGS. 4(a) and 4(b) show the example in which the 24 magnetoresistive sensor parts 105-1 to 105-24 are arranged on the substrate 401. When the magnetoresistive sensor parts 105 have parallelepiped shapes and the sensitivity direction perpendicular to the plane of paper as shown in FIGS. 4(a) and 4(b), for example, in order to place as many magnetoresistive sensor parts 105 as possible, they are arranged on the substrate 401 having a size of a diameter of about 15 mm so that the sensitive directions of the magnetic fields may be the same.

The arrangement example of the magnetoresistive sensor parts 105 shown in FIG. 4 is common among all of the following embodiments and will not be explained in the following embodiments, however, the same configuration may be applied to all embodiments.

Embodiment 2

In embodiment 1, when the number of the parallel-connected magnetoresistive sensor parts 105 is increased, the thermal noise Vr generated from the resistance of the magnetoresistive sensor parts 105 is smaller. As the thermal noise Vr decreases with the increase of the number of parallel connections, the voltage noise Va of the preamplifier 103 is gradually predominant in the entire noise. In embodiment 2 of the invention, a technique of reducing the voltage noise Va of the preamplifier 103 that becomes obvious by employing the configuration explained in embodiment 1 will be explained.

The system noise Vn of the MR sensor 100 can be expressed by the following formula 2. As shown in formula 2, regarding the system noise Vn, when the thermal noise Vr due to the resistance of the magnetoresistive sensor parts 105 is smaller, the voltage noise Va of the preamplifier 103 is predominant. In the embodiment 2, as a method of reducing the voltage noise Va of the preamplifier 103, a configuration in which a plurality of the preamplifiers 103 are parallel-connected is employed.

$$Vn=(Vr^2+Va^2)^{1/2} \quad \text{formula 2}$$

FIG. 5 is a circuit diagram of the MR sensor 100 according to the embodiment 2. In the embodiment 2, the preamplifiers 103 are provided for the respective magnetoresistive sensor parts 105 and the outputs of the respective magnetoresistive sensor parts 105 are input to the respective corresponding preamplifiers 103. The outputs of the respective preamplifiers 103 are parallel connected by an adder, and input to an amplifier 501.

When the N preamplifiers 103 are parallel connected, the voltage noise Va of the preamplifiers 103 decreases to one $N^{1/2}$th as a whole. In the configuration shown in FIG. 5, the four preamplifiers 103 are parallel connected, and the voltage noise of the preamplifiers 103 decreases to one $4^{1/2}$th=one half as a whole. As described above, also the preamplifiers 103 are parallel connected in addition to the magnetoresistive sensor parts 105, and thereby, the system noise Vn expressed in formula 2 may be integrally reduced.

FIG. 6 shows measurement results of the system noise measured using an actual AMR sensor with respect to the MR sensor 100 according to the embodiment 2. Sign 601 denotes system noise measured using the configuration in FIG. 1 and sign 602 denotes system noise measured using the configuration in FIG. 5. Signs 603 and 604 denote white noise in the respective measurement results. The white noise 603 was 35 $pT/Hz^{1/2}$ and the white noise 604 was 17 $pT/Hz^{1/2}$.

According to the measurement results shown in FIG. 6, it is known that the white noise 604 is decreased to be lower than the white noise 304 shown in FIG. 3. That is, as expressed in the theoretical formula of the formula 2, it is known that the preamplifiers 103 are parallel-connected and the voltage noise Va of the preamplifiers 103 is reduced, and thereby, the system noise can be reduced to be about one half or less as a whole.

Embodiment 3

In embodiments 1 and 2, the magnetoresistive sensor parts 105 are parallel-connected and the preamplifiers 103 are further parallel-connected, and thereby, the white noise of the system noise may be reduced. However, as shown in FIG. 6, there is a problem that 1/f noise at 10 Hz or less remains higher. It is considered that this is because the white noise is reduced by parallel connection of the magnetoresistive sensor parts 105, and the 1/f noise becomes obvious. Accordingly, in embodiment 3 of the invention, a method of reducing the 1/f noise using set/reset signals will be explained.

FIG. 7 is a circuit diagram of an MR sensor 100 according to the embodiment 3. In addition to the configurations explained in embodiments 1 and 2, the MR sensor 100 in the embodiment 3 includes set/reset circuits 701 for the respective magnetoresistive sensor parts 105. In FIG. 7, the circuit configuration in which the set/reset circuits 701 are provided in addition to the circuit configuration of embodiment 1 is exemplified, however, the same configuration may be provided in embodiment 2 and the number of magnetoresistive sensor parts 105 is not limited to four.

In the configuration shown in FIG. 7, the set/reset circuits 701-1 to 701-4 are provided in correspondence with the four magnetoresistive sensor parts 105-1 to 105-4, respectively, and the respective set/reset circuits 701-1 to 701-4 are parallel-connected.

An alternating-current signal generator 703 supplies an alternating current (several kilohertz to several tens of kilohertz) to the respective set/reset circuits 701-1 to 701-4. The respective set/reset circuits 701-1 to 701-4 include coils that generate magnetic fields using the alternating current and apply them to the magnetoresistive elements 101. The circuits are adapted so that, when the magnetic fields are applied to the magnetoresistive elements 101, the magnetization directions of the magnetoresistive elements 101 may be the same direction. Therefore, the magnetization directions of the magnetoresistive elements 101 are changed by the alternating current in response to its frequency, and thereby, an effect of cancelling the 1/f noise due to fluctuations in magnetization direction may be exhibited.

The output of the preamplifier 103 is connected to a lock-in amplifier 702. The lock-in amplifier 702 detects the output of the preamplifier 103 using the alternating current or a synchronizing signal (TTL signal) output by the alternating-current signal generator 703 as a reference signal 704, and outputs a detection result from the output terminal 104.

FIG. 8 shows measurement results of system noise measured using an actual AMR sensor with respect to the MR sensor 100 according to the embodiment 3. Sign 801 denotes system noise measured using the configuration in FIG. 1 and sign 802 denotes system noise measured using the configuration in FIG. 7. Signs 803 and 804 denote white noise in the respective measurement results. The white noise 803 was 35 pT/Hz$^{1/2}$ and the white noise 804 was 20 pT/Hz$^{1/2}$. That is, the same effect as that of embodiment 1 was obtained with respect to white noise.

Further, compared to the measurement results of embodiment 1 shown in FIG. 3, it is known that the system noise 802 is also lower in the low-frequency region (10 Hz or less), and the 1/f noise is reduced in this region.

As described above, the MR sensor 100 according to the embodiment 3 may reduce the white noise by parallel connection of the magnetoresistive sensor parts 105, reduce the 1/f noise that becomes obvious thereby using the set/reset circuits 701, and improve the sensitivity to the level at which the biomagnetic field can be measured.

Embodiment 4

In the configuration explained in embodiment 3, it is considered that the preamplifiers 103 are parallel-connected like embodiment 2 for reduction of the thermal noise Va of the preamplifiers 103. However, for example, when about ten or more preamplifiers 103 are parallel-connected, more power is consumed and more heat is generated, and thereby, the preamplifiers 103 are more likely to oscillate. Further, preamplifier current noise In flows to the magnetoresistive sensor parts 105 in the amount corresponding to the number of preamplifiers 103, and voltage noise is generated due to the resistance of the magnetoresistive sensor parts 105. Furthermore, in consideration of mounting of the preamplifiers 103 on the substrate 401, provision of many preamplifiers 103 is impractical. Accordingly, in embodiment 4 of the invention, a configuration in which a plurality of magnetoresistive sensor parts 105 are parallel-connected and only one preamplifier 103 is provided for reduction of the noise of the preamplifier 103 will be explained.

FIG. 9 is a circuit diagram of an MR sensor 100 according to the embodiment 4. The MR sensor 100 in the embodiment 4 includes a step-up transformer 901 between the magnetoresistive sensor parts 105 and the preamplifier 103. The respective magnetoresistive sensor parts 105 are parallel-connected to the primary side of the step-up transformer 901, and the secondary side is input to the preamplifier 103. The rest of the configuration is the same as that of embodiment 3.

The magnetization direction of the magnetoresistive sensor part 105 is inverted in response to the frequency of the alternating-current signal generator 703 by the action of the set/reset circuit 701, and the output of the magnetoresistive sensor part 105 is an alternating-current signal. The step-up transformer 901 uses this to boost the output of the magnetoresistive sensor part 105.

For example, the step-up transformer 901 forms a ten-fold amplification booster circuit using 100-turn winding at the primary side and 1000-turn winding at the secondary side, and thereby, the noise of the preamplifier 103 may be made effectively negligible. It is necessary to make the resistance value of the primary-side winding of the step-up transformer 901 sufficiently smaller than the resistance between both sides of the magnetoresistive sensor part 105 and suppress the influence of white noise by the primary-side winding resistance. Further, it is necessary to set the inductance of the primary-side winding to be sufficiently higher to make the impedance of the alternating-current signals higher so that the outputs of the respective magnetoresistive sensor parts 105 may not be short-circuited as the alternating-current signals. Accordingly, as the core of the step-up transformer 901, a member with higher permeability such as ferrite is desirably used.

FIG. 10 shows measurement results of system noise measured using an actual AMR sensor with respect to the MR sensor 100 according to the embodiment 4. Sign 1001 denotes system noise measured using the configuration in FIG. 1 and sign 1002 denotes system noise measured using the configuration in FIG. 9. Signs 1003 and 1004 denote white noise in the respective measurement results. The white noise 1003 was 35 pT/Hz$^{1/2}$ and the white noise 1004 was 17 pT/Hz$^{1/2}$.

In comparison with the measurement results shown in FIG. 8, it is known that the equal effect to that of embodiment 3 was obtained with respect to 1/f noise, and further, the white noise is reduced to be lower than that of embodiment 3. This is considered to be the effect by the reduction of the voltage noise of the preamplifier 103 by the step-up transformer 901.

As described above, the input to the preamplifier 103 is amplified in advance by the step-up transformer 901 using the alternating-current signals generated using the set/reset circuits 701, and thereby, the noise of the preamplifier 103 may be relatively reduced and, even when only one preamplifier 103 is provided, the influence of the noise may be effectively suppressed. Thereby, the configuration of the preamplifier 103 is simpler and the oscillation may be suppressed and the power consumption may be suppressed.

The amplification by the step-up transformer 901 is possible if the input to the step-up transformer 901 is the alternating-current signal, and thus, it is considered that, in place of the set/reset circuits 701, the direct-current power source 102 is replaced by an alternating-current power source. Note that, in the configuration, the noise of the preamplifier 103 may be suppressed by the effect of the step-up transformer 901, but the magnetization directions of the magnetoresistive elements 101 remain fixed. Therefore, it is necessary to note that the effect of reducing the 1/f noise due to fluctuations is not exerted.

Embodiment 5

In embodiments 1 to 4, the configurations for reduction of white noise and 1/f noise are explained. However, the actual measuring object may be e.g., an object having a temperature like a living organism or a metal material for non-destructive inspection (with higher heat conductivity). In this case, the temperatures of the magnetoresistive sensor parts 105 differ depending on the locations in which they are placed and the sensitivity of the respective magnetoresistive sensor parts 105 varies due to temperature fluctuations, and thus, the 1/f noise and the white noise may increase. The fluctuations in sensor sensitivity are generated due to temperature disturbance different from that due to the circuit configuration itself, and thus, it is considered that it is necessary to separately provide a configuration for suppressing that. Accordingly, in embodiment 5 of the invention, a configuration of suppressing the above described fluctuations in sensor sensitivity will be explained.

FIG. 11 is a circuit diagram of an MR sensor 100 according to the embodiment 5. The MR sensor 100 in the embodiment 5 includes a feedback circuit in addition to the configurations explained in embodiments 1 to 4. In FIG. 11, a configuration in which the feedback circuit is provided in addition to the circuit configuration explained in embodiment 4 is exemplified, however, the feedback circuit may be provided in the circuit configurations of the other embodiments.

The feedback circuit is a circuit that feeds back the output of the preamplifier 103 to the magnetoresistive elements 101 as the magnetic field applied to the magnetoresistive elements 101, and has a feedback resistor 1101 and feedback coils 1102.

The feedback coils 1102 are provided the respective magnetoresistive sensor parts 105 (feedback coils 1102-1 to 1102-4 in FIG. 11), receive signals between the output of the preamplifier 103 and the input of the lock-in amplifier 702, generate magnetic fields using them, and feed them back to the magnetoresistive elements 101. The feedback resistor 1101 is provided between the output of the preamplifier 103 and the feedback coils 1102. In FIG. 11, the respective feedback coils 1102 are parallel-connected, however, they may be series-connected.

When the phase of the signals output by the set/reset circuits 701 differs according to the inductance of the step-up transformer 901, a phase adjustment circuit may be inserted at the downstream of the feedback circuits 1102, at the downstream of the preamplifier 103 or in the step-up transformer 901 itself for adjustment.

The feedback circuits are provided and the output of the preamplifier 103 is fed back to the magnetoresistive elements 101, and thereby, the influences of the temperature differences depending on the positions of the magnetoresistive sensor parts 105 and the sensitivity fluctuations due to the temperature of the measuring object may be suppressed. For example, the configuration is effective when the magnetoresistive sensor parts 105 are planarly (spatially) arranged and the temperatures differ in the respective magnetoresistive sensor parts 105.

Sixth Embodiment

In the step-up transformers 901 explained in embodiments 4 and 5, it is necessary to make the winding impedance higher as explained in embodiment 4. For the purpose, it is necessary to use a member having a larger size of several centimeters or more with higher permeability as the core of the step-up transformer 901. It is difficult to wind 1000 turns or more of the secondary winding in the step-up transformer 901 with the larger core in consideration of attachment to the substrate 401 shown in FIG. 4. Accordingly, in embodiment 6 of the invention, a configuration in which the amplification factor is improved while the size of the step-up transformer 901 is suppressed will be explained.

FIG. 12 is a circuit diagram of an MR sensor 100 according to the embodiment 6. In the embodiment 6, a capacitor 1201 forming a resonance circuit with the secondary-side coil is provided at the secondary side of the step-up transformer 901. By the secondary-side inductance of the step-up transformer 901 and the capacitor 1201, resonance is generated at the frequency of the alternating-current signal generator 703 (or the frequency of the alternating-current power source for driving the magnetoresistive sensor parts 105). Thereby, the amplification factor is improved to be equal to or more than the winding ratio of the step-up transformer 901 (the ratio in number of turns between the primary winding and secondary winding).

Embodiment 7

The step-up transformers 901 explained in embodiments 4 to 6 are effective for reducing noise of the preamplifier 103, however, it may be possible that problems such that the size (several centimeters) of the step-up transformer 901 is larger, the phase adjustment is more complicated, and the preamplifier 103 is more likely to oscillate. Accordingly, in embodiment 7 of the invention, a configuration of reducing the noise of the preamplifier 103 without using the step-up transformer 901 will be explained.

FIG. 13 is a circuit diagram of an MR sensor 100 according to the embodiment 7. The MR sensor 100 in the embodiment 7 includes additional positive feedback (hereinafter, abbreviated as APF) circuits in addition to the configuration explained in embodiment 3. The APR circuit has an APF resistor 1301 and an APF coil 1302. One APF coil 1302 is provided for each of the magnetoresistive sensor parts 105 (APF coils 1302-1 to 1302-4 in FIG. 13). The APF coil 1302 generates a magnetic field applied to the magnetoresistive elements 101. The APF resistors 1301 is provided for each of the APF coils 1302 and series-connected to each of the APF coils 1302.

The APF coils 1302 are magnetically coupled to the magnetoresistive sensor parts 105 and feed back the outputs of the magnetoresistive sensor parts 105 as the magnetic fields applied to the magnetoresistive elements 101 to the magnetoresistive elements 101 via the APF resistors 1301. The APF circuits are provided, and thereby, the magnetic field-voltage conversion efficiency of the magnetoresistive sensor parts 105 is raised and the noise of the preamplifier 103 may be effectively reduced. Only one APF resistor 1301 may be provided in common among the respective APF coils 1302.

The APF resistor 1301 generates thermal noise and is necessary to have a sufficiently lower value than the resistance between both ends of the magnetoresistive sensor part 105. When the resistance value of the APF resistor 1301 is smaller (e.g., about 10Ω), a configuration that the inductance of the APF coil 1302 is made larger so that the output of the magnetoresistive sensor part 105 may not be short-circuited should be formed, and therefore, it is necessary to make the impedance of the APF coil 1302 higher at the frequency of the alternating-current signal generator 703. It is necessary to make the impedance of the APF coil 1302 at least larger than the resistance between both ends of the magnetoresistive sensor part 105.

As described above, the APF circuits that feed back the outputs of the magnetoresistive sensor parts 105 as the magnetic fields applied to the magnetoresistive elements 101 to the magnetoresistive elements 101 is provided, and thereby, the noise of the preamplifier 103 may be substantially reduced without the step-up transformer 901. Thereby, the equal effect to that of the step-up transformer 901 may be exhibited by the simpler and smaller circuit configuration.

Embodiment 8

FIG. 14 is a circuit diagram of an MR sensor 100 according to embodiment 8 of the invention. The MR sensor 100 in the embodiment 8 has a configuration using both the feedback circuit explained in embodiments 5 and 6 and the APF circuits explained in embodiment 7. As shown in FIG. 14, the APF coils 1302 also serve as the feedback coils 1102 and the APF resistors 1301 also serve as the feedback resistors 1101, and thereby, this is realized. Note that it is necessary to connect the feedback circuits to both the outputs of the magnetoresistive sensor parts 105 and the output of the preamplifier 103.

If allowed in view of the mounting area of the circuits, the APF coils 1302 may not serve as the feedback circuits 1102, but the coils may be individually provided. The same applies to the APF resistors 1301 and the feedback resistors 1101.

The APF circuits and the feedback circuits are provided within the same drive circuit, and thereby, the system noise may be reduced by the simpler circuit configuration, and further, the influences of the temperature differences depending on the positions of the magnetoresistive sensor parts 105 and the temperature of the measuring object may be suppressed.

Embodiment 9

The system noise may be reduced using the configurations of the MR sensors 100 explained in embodiments 1 to 8 and the sensitivity that enables measurement of the biomagnetic field may be obtained. On the other hand, the MR sensor 100 having the higher sensitivity detects extraneous interfering magnetic fields generated from automobiles, electric railcars, etc. more easily, and it may be harder to detect only the biomagnetic field components. Accordingly, in embodiment 9 of the invention, a configuration of a gradiometer that employs the MR sensors 100 explained in embodiments 1 to 8 are employed, and may efficiently reduce the interfering magnetic fields and measure the biomagnetic field with high sensitivity will be explained.

FIG. 15 shows a configuration of a gradiometer 1500 according to the embodiment 9. The gradiometer 1500 includes sensor units 1501 and 1502 and a preamplifier 1503. Each of the sensor units 1501 and 1502 is formed by parallel connection of a plurality of the MR sensors 100 explained in some of the embodiments 1 to 8. Here, the configuration in which the MR sensors 100-1 to 100-4 and 100-5 to 100-8 are parallel-connected is exemplified, however, the number of the MR sensors 100 is not limited to that. The preamplifier 1503 amplifies the difference between the respective outputs of the sensor units 1501 and 1502, and outputs it from an output terminal 1504.

The sensor units 1501 and 1502 are provided in spatially different locations. The respective outputs of the sensor units in the two locations are amplified by the preamplifier 1503, and thereby, the number of magnetoresistive sensor parts 105 is doubled and the system noise generated from the resistance of the magnetoresistive sensor parts 105 may be reduced to one $2^{1/2}$th.

A direct-current power source 102-1 contained in the sensor unit 1501 and a direct-current power source 102-2 contained in the sensor unit 1502 are formed to have opposite polarity to each other. Thereby, the measurement magnetic field directions of the respective sensor units are opposite, and a magnetic sensor that measures the differential magnetic field, i.e., a gradiometer may be formed.

In FIG. 15, the configuration with the two sensor units is exemplified, however, the number of sensor units is not limited to that. For example, an active shield with one sensor unit provided farther from the measuring object that feeds back the measurement result to a plurality of sensor units for biomagnetic field detection to cancel the interfering magnetic fields may be formed.

The invention is not limited to the above described embodiments, but includes various modified examples. The above described embodiments are explained in detail for clear explanation of the invention, but not necessarily limited to those including all of the explained configurations. Further, part of the configuration of the embodiment may be replaced by the configuration of the other embodiment. Furthermore, the configuration of the embodiment may be added to the configuration of the other embodiment. In addition, with respect to part of the configuration of each embodiment, addition, deletion, and replacement may be performed by other configurations.

REFERENCE SIGNS LIST

100: MR sensor, 101: magnetoresistive element, 102: direct-current power source, 103: preamplifier, 104: output terminal, 105: magnetoresistive sensor part, 401: substrate, 402: connector part, 501: amplifier, 701: set/reset circuit, 702: lock-in amplifier, 703: alternating-current signal generator, 704: reference signal, 901: step-up transformer, 1101: feedback resistor, 1102: feedback coil, 1201: capacitor, 1301: APF resistor, 1302: APF coil, 1500: gradiometer, 1501 and 1502: sensor units, 1503: preamplifier, 1504: output terminal.

What is claimed is:

1. A magnetoresistive sensor comprising:
    a plurality of magnetoresistive sensor parts each having a bridge circuit in which four magnetoresistive elements are connected;
    an amplifier circuit that amplifies outputs of the magnetoresistive sensor parts, wherein the outputs of the respective magnetoresistive sensor parts are connected in parallel to one another to an input of the amplifier circuit; and
    a set/reset circuit that generates set pulse and reset pulse for inverting magnetization of the magnetoresistive elements; and a detection circuit that detects an alternating-current signal output by the magnetoresistive sensor part using the set pulse and reset pulse generated by the set/reset circuit.

2. The magnetoresistive sensor according to claim 1, further comprising a step-up transformer that boosts an output voltage of the magnetoresistive sensor part between the output of the magnetoresistive sensor part and the amplifier circuit, wherein the outputs of the respective magnetoresistive sensor parts are connected in parallel to one another to the step-up transformer.

3. The magnetoresistive sensor according to claim 1, further comprising a feedback circuit that feeds back the output of the amplifier circuit to the magnetoresistive elements as a magnetic field applied to the magnetoresistive elements.

4. The magnetoresistive sensor according to claim 2, further comprising a capacitor that forms a resonance circuit with inductance of a secondary-side coil of the step-up transformer.

5. The magnetoresistive sensor according to claim 1, further comprising an additional positive feedback circuit that feeds back the output of the magnetoresistive sensor part to the magnetoresistive elements as a magnetic field applied to the magnetoresistive elements.

6. The magnetoresistive sensor according to claim 5, wherein the additional positive feedback circuit has a coil that generates the magnetic field, and impedance of the coil is larger than resistance between both ends of the magnetoresistive sensor part.

7. The magnetoresistive sensor according to claim 6, further comprising a feedback circuit that feeds back the output of the amplifier circuit to the magnetoresistive elements as a magnetic field applied to the magnetoresistive elements.

8. A gradiometer comprising: first and second magnetoresistive sensors according to claim 1; and a third amplifier circuit that amplifies differences between outputs of the respective magnetoresistive sensor parts.

9. The gradiometer according to claim 8, further comprising: a first direct-current power source that applies a direct-current voltage to the first magnetoresistive sensor; and a second direct-current power source that applies a direct-current voltage to the second magnetoresistive sensor, wherein polarity of the first direct-current power source is set to be opposite to polarity of the second direct-current power source, and an output of the first magnetoresistive sensor and an output of the second magnetoresistive sensor are respectively input to the third amplifier circuit.

\* \* \* \* \*